United States Patent
Cournoyer et al.

(10) Patent No.: US 9,498,208 B2
(45) Date of Patent: *Nov. 22, 2016

(54) METHODS FOR PASSING MULTIPLE SUTURES THROUGH TISSUE

(71) Applicant: DePuy Mitek, LLC, Raynham, MA (US)

(72) Inventors: John R. Cournoyer, Norfolk, VA (US); Howard C. Tang, Boston, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,776

(22) Filed: Jan. 20, 2016

(65) Prior Publication Data
US 2016/0135804 A1  May 19, 2016

Related U.S. Application Data

(63) Continuation of application No. 13/731,323, filed on Dec. 31, 2012, now Pat. No. 9,271,722.

(51) Int. Cl.
*A61B 17/04* (2006.01)
*A61B 17/062* (2006.01)
*A61B 17/29* (2006.01)
*A61B 17/06* (2006.01)

(52) U.S. Cl.
CPC ....... *A61B 17/0469* (2013.01); *A61B 17/0401* (2013.01); *A61B 17/0483* (2013.01); *A61B 17/0485* (2013.01); *A61B 17/0491* (2013.01); *A61B 17/0625* (2013.01); *A61B 17/29* (2013.01); *A61B 2017/06042* (2013.01); *A61B 2017/06095* (2013.01)

(58) Field of Classification Search
CPC .......... A61B 17/0401; A61B 17/0469; A61B 17/0482; A61B 17/0483; A61B 17/0491; A61B 17/0625; A61B 17/29
See application file for complete search history.

(56) References Cited

U.S. PATENT DOCUMENTS

| | | |
|---|---|---|
| 5,318,577 A | 6/1994 | Li |
| 5,730,747 A | 3/1998 | Ek et al. |
| 5,947,982 A | 9/1999 | Duran |
| 6,896,686 B2 | 5/2005 | Weber |
| 6,984,237 B2 | 1/2006 | Hatch et al. |
| 7,377,926 B2 | 5/2008 | Topper et al. |

(Continued)

OTHER PUBLICATIONS

DePuy Mitek ExpresSew II Surgical Technique Guide. DePuy Mitek, Inc. 2007. 8 pages.

(Continued)

*Primary Examiner* — Ashley Fishback

(57) ABSTRACT

Methods for passing multiple sutures through tissue are provided herein. In particular, the methods described herein allow multiple sutures to be passed through tissue without removing a suture passing instrument from a patient's body. In one embodiment, a method for passing a suture through tissue is provided that includes loading first and second suture limbs into a suture passing instrument, positioning the instrument within a patient's body, actuating the instrument to pass a portion of the first suture limb through the tissue, pulling the first suture limb through the tissue, pulling the second suture limb to reload the suture passing instrument without removing the instrument from the patient's body, actuating the instrument a second time to pass a portion of the second suture limb through the tissue, and pulling the second suture limb through the tissue.

18 Claims, 16 Drawing Sheets

(56) References Cited

U.S. PATENT DOCUMENTS

| | | |
|---|---|---|
| 7,381,212 B2 | 6/2008 | Topper et al. |
| 7,654,321 B2 | 2/2010 | Zazovsky et al. |
| 7,879,046 B2 | 2/2011 | Weinert et al. |
| 7,972,344 B2 | 7/2011 | Murray et al. |
| 2001/0018592 A1* | 8/2001 | Schaller ............. A61B 17/0469 606/151 |
| 2003/0065337 A1 | 4/2003 | Topper et al. |
| 2003/0139752 A1* | 7/2003 | Pasricha ............ A61B 17/0482 606/139 |
| 2005/0288690 A1 | 12/2005 | Bourque et al. |
| 2008/0033486 A1* | 2/2008 | Whittaker .......... A61B 17/0401 606/232 |
| 2010/0121352 A1 | 5/2010 | Murray et al. |
| 2014/0188136 A1 | 7/2014 | Cournoyer et al. |

OTHER PUBLICATIONS

DePuy Mitek ExpresSew III Surgical Technique Guide. DePuy Mitek, Inc. 2011. 8 pages.

* cited by examiner

METHODS FOR PASSING MULTIPLE SUTURES THROUGH TISSUE

FIELD

The present application claims priority to U.S. patent application Ser. No. 13/731,323 entitled "Methods for Passing Multiple Sutures Through Tissue" filed Dec. 31, 2012, which is hereby incorporated by reference in its entirety.

BACKGROUND

Many surgical procedures require fixing tissue with respect to bone, artificial anchors, or other tissue using sutures. A variety of stitches are known that can be utilized to position and fix a portion of tissue at a desired location. However, passing sutures through tissue to create one or more stitches can be challenging due to the confined working space of a patient's body and the limited accessibility of the tissue. This is especially true in minimally invasive surgical procedures that require surgical tools to be inserted into a patient's body through small diameter cannulas, thereby preventing a user from directly manipulating a suture or tissue.

Several suture passing instruments have been developed in response to these and other challenges that allow a user to grasp a portion of tissue and pass a suture through the grasped tissue. The portion of the suture passed through the tissue can then be grasped with a second tool and further manipulated. One example of a suture passing instrument is described in U.S. Pat. No. 7,879,046 to Weinert et al., entitled "Suturing Apparatus and Method," the contents of which are hereby incorporated by reference in their entirety. A number of other suture passing instruments are also known in the art.

One challenge faced by users of suture passing instruments is the need to repeatedly remove the instrument from a patient's body for reloading. As mentioned above, a variety of stitches are known that can be used in positioning and fixing tissue, and most stitches require passing multiple portions of one or more suture strands through tissue at one or more locations. Using known devices and methods, a user loads a single suture into a suture passing instrument, inserts and positions the instrument within a patient's body, passes the suture through tissue, and removes the instrument from the patient's body to repeat these steps for each additional suture that must be passed through tissue.

The repeated insertion and removal of the suture passing instrument from the patient's body can introduce a number of challenges. For example, sutures passed through tissue often have a free end extending through the cannula used to insert the suture passing instrument so that a user can further manipulate the suture during the procedure. Repeatedly removing the suture passing instrument and reintroducing it through the cannula can risk snagging or entangling the instrument with one or more of the suture free ends extending through the cannula. Furthermore, removing and reintroducing the suture passing instrument can distort a user's frame of reference for creating a stitching pattern because the instrument must be positioned anew for each suture passing. Still further, in some procedures it can be desirable to pass multiple sutures through a single hole in tissue. It is difficult to reposition the suture passing instrument after removing it from the body for reloading such that a second suture can be passed through the same hole as a first suture. These challenges add time and difficulty to surgical procedures that require passing multiple sutures through tissue.

Accordingly, there is a need for novel methods for passing multiple sutures through tissue in a more efficient manner. In particular, there is a need for improved methods for loading and utilizing existing suture passing instruments to pass multiple sutures through tissue and reduce the challenges associated with repeatedly inserting and removing a suture passing instrument from a patient's body.

SUMMARY

The present invention generally provides methods for passing multiple sutures through tissue. In particular, the methods described herein pass multiple sutures through tissue without having to remove a suture passing instrument from a patient's body to reload the instrument. The methods described herein can utilize existing suture passing instruments and address several challenges encountered by users of these prior art devices. For example, the methods described herein double-load a suture passing instrument with suture limbs that can be opposite ends of a single strand of suture, or two ends of separate suture strands. Using the methods described herein, a user can insert the instrument into a patient's body and pass both suture limbs through tissue without having to remove the instrument from the patient's body for reloading. To do this, the methods described herein provide a novel remote reloading process accomplished by manipulating a free end of one of the suture limbs loaded in the instrument. The methods described herein can be utilized to create a number of different stitches in tissue, including, for example, an inverted mattress stitch. Such a stitching pattern can be useful in a variety of surgical procedures, including, for example, the repair of a rotator cuff tear in a patient's shoulder.

Reducing the number of times that a user removes a suture passing instrument for reloading can have a number of advantages. These can include, for example, reducing the possibility of snagging or entangling the suture passing instrument on previously-passed suture strands that extend through a cannula used to introduce the instrument, reducing the difficulty level of a procedure, reducing the time required for a procedure, etc. In addition, by passing multiple sutures without removing the device from a patient's body, a frame of reference can be created between consecutive suture passes, thereby allowing for more accurate and easier repositioning of the suture passing instrument. Still further, the methods described herein allow multiple sutures to be passed through a single hole formed in tissue, which can be desirable in a number of procedures.

In one aspect, a method of passing a suture through tissue is provided that includes loading a first suture limb into a retaining mechanism disposed at a distal end of a suture passing instrument such that the first suture limb extends on a first side of the instrument. The first side of the instrument can be any side or surface but, in some embodiments, can be a bottom surface of the instrument. The method further includes loading a second suture limb into the retaining mechanism of the suture passing instrument such that the second suture limb extends on the first side of the instrument. The method also includes positioning first and second jaws of the suture passing instrument to grasp tissue within a patient's body, and deploying a needle from the suture passing instrument such that the needle extends through the tissue grasped between the first and second jaws of the instrument. The needle carries a portion of at least the first suture limb through the tissue such that the first and second suture limbs extend from a first tissue surface and at least a first suture loop is formed on a second tissue surface opposite the first tissue surface. The method further includes pulling the first suture loop to draw the first suture limb through the tissue, and pulling the second suture limb toward a proximal end of the suture passing instrument to draw the second suture limb into a proximal end of the retaining mechanism without removing the suture passing instrument from the patient's body. The method also includes deploying the needle from the suture passing instrument a second time to carry a portion of the second suture limb through the tissue such that the second suture limb extends from the first tissue surface and a second suture loop is formed on the second tissue surface, and pulling the second suture loop to draw the second suture limb through the tissue.

The methods described herein can include a number of additional steps or variations that are considered within the scope of the present invention. For example, in some embodiments, the second suture limb can be loaded into the retaining mechanism such that it can extend outside the patient's body when the suture passing instrument is inserted into the patient's body. This can result in the second suture limb extending farther from the suture passing instrument than the first suture limb. By way of further example, in some embodiments that first suture limb can extend from the suture passing instrument by about 10-20 mm and the second suture limb can extend from the suture passing instrument by about 250 mm.

In certain embodiments, positioning the first and second jaws of the suture passing instrument can include inserting the instrument into a patient's body, opening the jaws to receive tissue therebetween, and closing the jaws to grasp the tissue. Furthermore, in some embodiments, the instrument can be inserted into the patient's body through a cannula.

In other embodiments, the method can further include retracting the needle following deployment such that the needle retracts into the suture passing instrument without moving the first or second suture limbs. The retraction of the needle can ensure that the needle does not damage adjacent tissue and also leaves the one or more suture loops formed on the second tissue surface more accessible to be grasped and manipulated.

In still other embodiments, the method can further include, prior to pulling the first suture loop, determining which of two suture loops is the first suture loop by pulling the second suture limb toward a proximal end of the suture passing instrument to reduce the size of a second suture loop formed on the second tissue surface. In particular, pulling on the second suture limb can reduce the size of one of the two suture loops formed on the second tissue surface, thereby allowing a user to differentiate between the first and second suture loops.

In some embodiments, the method can further include at least partially opening the first and second jaws prior to pulling the second suture limb toward a proximal end of the instrument to permit easier movement of the second suture limb with respect to the retaining mechanism. Opening the jaws can reduce the amount of force necessary to pull the second suture limb into the proximal-most portion of the retaining mechanism. Seating the second suture limb without opening the jaws is possible as well, however. In addition, in some embodiments the jaws can be only partially opened such that the second suture limb can move more easily, but the tissue can still be relatively firmly grasped by the first and second jaws such that the suture passing instrument does not move with respect to the tissue.

In certain embodiments, the method can further include repositioning the suture passing instrument without removing the instrument from the patient's body before deploying the needle a second time such that the second suture limb is passed through tissue at a different location than the first suture limb. Repositioning the suture passing instrument between each deployment of the needle can permit the creation of, for example, an inverted mattress stitch in the tissue. In some embodiments, repositioning the suture passing instrument can include opening the first and second jaws to release the tissue grasped therebetween, moving the instrument to receive a different portion of tissue between the first and second jaws, and closing the first and second jaws to grasp the different portion of tissue therebetween.

In some embodiments, however, the suture passing instrument may not be repositioned between the first and second deployments of the needle such that both the first and second suture limbs extend through a single hole formed in the tissue. Passing multiple suture limbs through a single hole in tissue can be utilized, for example, in combination with a helix bone anchor and/or spanning techniques across bone anchors used for rotator cuff repair.

In other embodiments, the method can further include attaching the second suture limb to a tensioning device that is coupled to the suture passing instrument at a location proximal to the retaining mechanism. The tensioning device can be configured to pull the second suture limb toward a proximal end of the instrument. Attaching the second suture limb to such a tensioning device can avoid the need to provide a longer second suture limb that can be manipulated by a user directly during a surgical procedure.

The methods described provide a great deal of utility and can be used in a variety of manners. For example, in some embodiments the method can further include attaching the first and second suture limbs to a bone anchor. This attachment can be performed before or after the suture limbs are passed through tissue. Further, in certain embodiments, the first and second suture limbs can be opposite ends of a single suture strand. Loading both ends of a single suture strand can create, for example, an inverted mattress stitch in tissue without removing the device from the patient's body. After forming the stitch, the free ends of the suture strand can be further manipulated (e.g., tied off to other strands, affixed to a bone anchor, etc.) and trimmed at the end of a procedure. In still other embodiments, the first and second suture limbs can be ends of separate suture strands, and the method can further include repeating the steps of the method recited above using the opposite ends of the separate suture strands as the first and second suture limbs. Utilizing the ends of separate suture strands as the first and second suture limbs, and repeating the method with the other ends of the separate strands, can create, for example, a double-width inverted mattress stitch in tissue with only one removal and reintroduction of the suture passing instrument.

In another aspect, a method of passing a suture through tissue is provided that includes loading first and second suture limbs into a retaining mechanism of a suture passing instrument such that the first and second suture limbs extend from a first side of the instrument, and inserting the suture passing instrument into the body of a patient. The method further includes positioning first and second jaws of the suture passing instrument to grasp tissue therebetween, and actuating the suture passing instrument to pass a portion of at least the first suture limb through the tissue grasped between the first and second jaws such that the first and second suture limbs extend from a first tissue surface and at least a first suture loop is formed on a second, opposite tissue surface. The method also includes pulling the first suture loop to draw the first suture limb through the tissue, and pulling the second suture limb toward a proximal end of the suture passing instrument to draw the second suture limb into a proximal end of the retaining mechanism without removing the suture passing instrument from the patient's body. The method further includes actuating the suture passing instrument a second time to pass a portion of the second suture limb through the tissue grasped between the first and second jaws such that the second suture limb extends from the first tissue surface and a second suture loop is formed on the second tissue surface, and pulling on the second suture loop to draw the second suture limb through the tissue.

In certain embodiments, the method can further include, prior to pulling the first suture loop, determining which of two suture loops is the first suture loop by pulling the second suture limb toward a proximal end of the suture passing instrument to reduce the size of a second suture loop formed on the second tissue surface.

In other embodiments, the method can further include repositioning the suture passing instrument without removing the instrument from the patient's body before actuating the instrument a second time such that the second limb is passed through tissue at a different location from the first suture limb.

Furthermore, in certain embodiments, the first and second suture limbs can be ends of separate suture strands, and the method can further include removing the instrument from the patient's body and repeating the method using the opposite ends of the separate suture strands as the first and second suture limbs.

In another aspect, a method for repairing a tear in tissue is provided that includes loading a first suture limb into a retaining mechanism disposed at a distal end of a suture passing instrument, the first suture limb having a free end and an opposite end anchored to bone within a patient's body. The method further includes loading a second suture limb into the retaining mechanism of the suture passing instrument, the second suture limb having a free end and an opposite end anchored to bone within a patient's body. The method also includes positioning first and second jaws of the suture passing instrument to grasp tissue within the patient's body, and actuating the suture passing instrument to pass a portion of the first suture limb through the tissue grasped between the first and second jaws such that a first suture loop is formed on a surface of the tissue. The method further includes pulling the first suture loop to draw the free end of the first suture limb through the tissue, and pulling the free end of the second suture limb toward a proximal end of the suture passing instrument to draw the second suture limb into a proximal end of the retaining mechanism without removing the suture passing instrument from the patient's body. The method also includes actuating the suture passing instrument a second time to pass a portion of the second suture limb through the tissue grasped between the first and second jaws such that a second suture loop is formed on the surface of the tissue. The method further includes pulling on the second suture loop to draw the free end of the second suture limb through the tissue, and anchoring the free ends of the first and second suture limbs to bone to secure the tissue with respect to the bone.

The method can have a number of variations or additional steps. In some embodiments, for example, anchoring the free ends of the first and second suture limbs to bone can include securing the free end of the first suture limb to a first bone anchor and the free end of the second suture limb to a second bone anchor. In other embodiments, the method can further include repositioning the suture passing instrument prior to actuating the suture passing instrument a second time. Repositioning the suture passing instrument in this manner can pass the free ends of the first and second suture limbs through the tissue at two different locations. In still other embodiments, the suture passing instrument need not be repositioned such that the free ends of the first and second suture limbs are passed through the tissue at a single location.

In certain embodiments, the method can also include repeating the steps of loading, positioning, and actuating the suture passing instrument with a third and a fourth suture limb that are also anchored at one end to bone in a patient's body. In such an embodiment, the method can also include anchoring the free ends of the third and fourth suture limbs to bone to secure the tissue with respect to the bone.

The method can be particularly suited to use in repairing tears in a patient's rotator cuff. In particular, the method can be used to span the first and second suture limbs through tissue and between a plurality of bone anchors. Accordingly, in certain embodiments, the tissue can be rotator cuff tissue and the bone can be the humerus.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the methods disclosed herein. One or more examples of these embodiments are illustrated in the accompanying drawings. Those skilled in the art will understand that the methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is generally directed to methods for passing sutures through tissue within a patient's body. In particular, the methods described herein pass multiple sutures through tissue without having to remove a suture passing instrument from the patient's body to reload the instrument. In one embodiment, this can be accomplished using a method for double-loading a suture passing instrument in combination with a method of remotely reloading the suture passing instrument after a first suture is passed through tissue. The method of reloading, described in more detail below, can include manipulating a free end of a suture limb loaded into the suture passing instrument from outside the patient's body.

Reducing the number of times a suture passing instrument is removed from and reintroduced into a patient's body during a procedure can have a number of advantages. For example, the overall difficulty of the procedure and the time required to complete it can be reduced due to a reduction in the number of steps required. In addition, the risk of snagging or entangling the suture passing instrument on previously-passed suture strands that extend through a cannula or percutaneous portal used to introduce the instrument can be reduced. Furthermore, the instrument can more easily be repositioned between consecutive suture passes, as a user's frame of reference will not be lost (i.e., the user will not become disoriented) by having to remove, reload, reintroduce, and reposition the instrument anew before passing a second suture through tissue. Still further, in some procedures it can be desirable to pass multiple sutures through a single hole formed in tissue (e.g., passing opposite ends of a single suture strand through a single hole to leave a loop on one side of tissue that can be affixed to an anchor, etc.). However, it is difficult to reposition a suture passing instrument to utilize a previously formed hole in tissue after removing the instrument from the patient's body to reload it. Using the methods described herein, multiple sutures can be passed at a single location without having to withdraw or reposition the instrument between passes.

Figure 1:
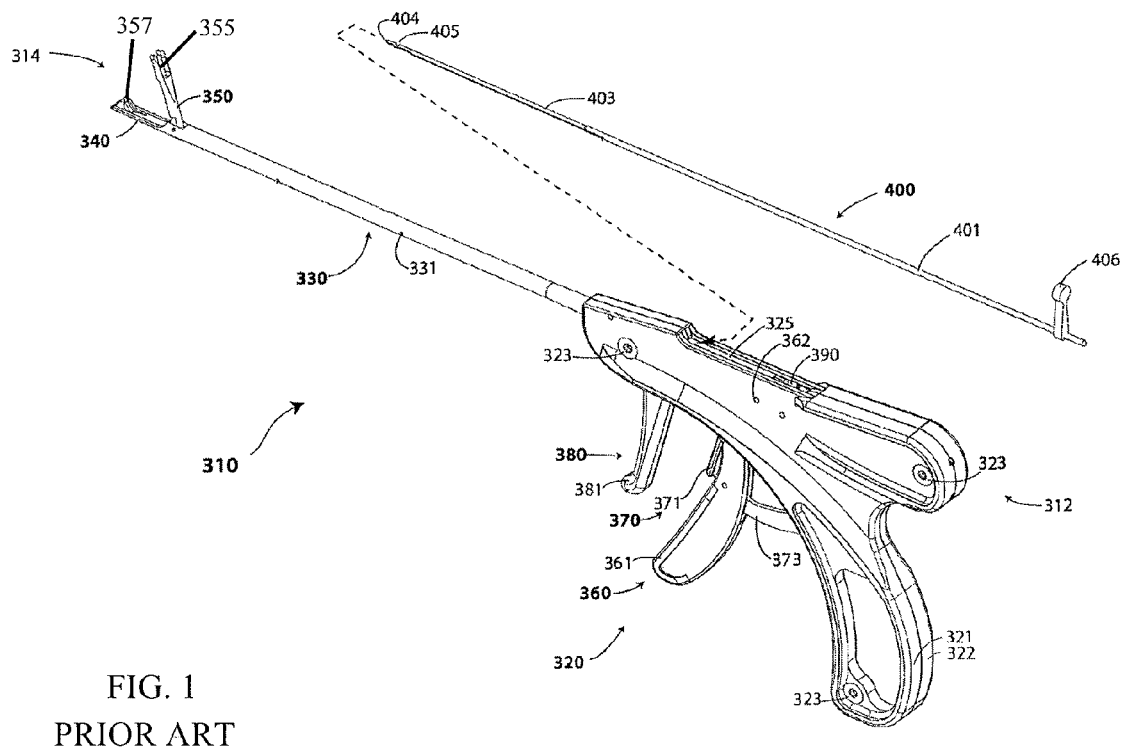
FIG. 1 is an illustration of one embodiment of a suture passing instrument.

Another advantage of the methods for passing multiple sutures described herein is that they can be used in combination with known suture passing instruments that have previously been configured to pass only a single suture before being removed from a patient's body for reloading. FIG. 1 illustrates one embodiment of a known suture passing instrument 310. The instrument 310 can include a set of first and second jaws 314 at a distal end thereof, and a handle assembly 320 at a proximal end 312 of the instrument. The jaws 314 and handle assembly 320 can be connected by an elongate shaft 330, thereby making the instrument suitably shaped for introduction into a patient's body through, for example, a small diameter cannula or percutaneous insertion portal during a minimally invasive surgical procedure.

The jaws 314 can include a lower fixed jaw 340 and an upper movable jaw 350. The lower fixed jaw 340 can be formed as an integral part of the elongate shaft 330 and can include a retaining mechanism (see FIGS. 2-4) that is configured to retain a portion of a suture loaded therein. The upper movable jaw 350 can be pivotally coupled to the lower jaw and can also be coupled to a jaw movement mechanism 360 in the handle assembly 320 such that movement of a trigger 361 can cause the movable jaw 350 to open or close. The movable jaw 350 can include an open portion 355 that can surround a protruded portion 357 of the lower jaw 340 when the jaws 314 are in a closed configuration.

A suture can be passed through tissue grasped between the jaws 314 using a bendable needle 400 that can extend from the handle assembly 320 to the jaws 314. The bendable needle can include a distal tip 404 configured to puncture tissue when deployed from the instrument, as well as a proximal and a distal needle body 401, 403. The needle can also include a notch 405 formed in a side thereof that can be configured to catch a suture loaded in the retaining mechanism of the lower jaw 340 and carry it through tissue grasped between the jaws 314. A proximal end of the needle 400 can be coupled to a needle movement mechanism 380 such that movement of a second trigger 381 can cause the needle 400 to deploy from the suture passing instrument or retract into the instrument.

Figure 2:
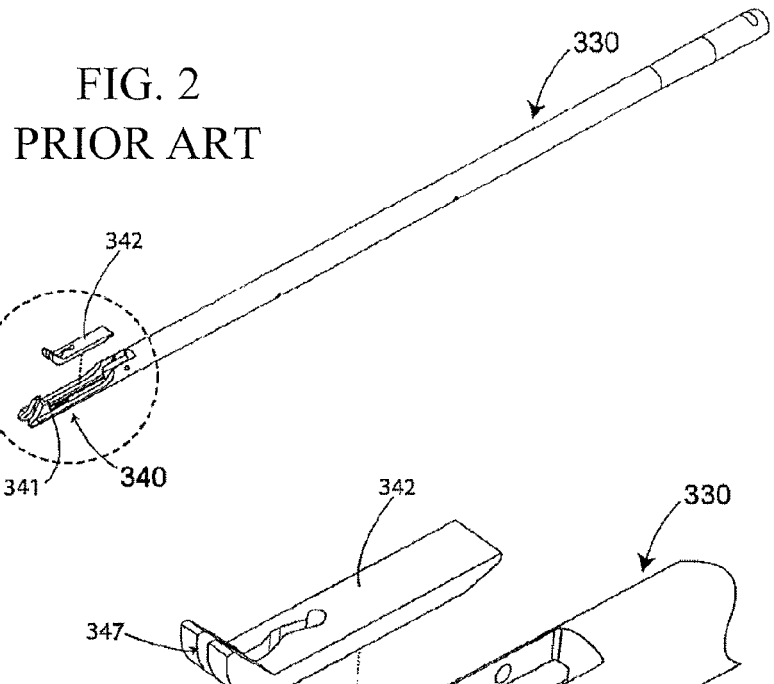
FIG. 2 is an exploded view illustration of an elongate shaft and lower jaw of the suture passing instrument of FIG. 1.
Figure 3:
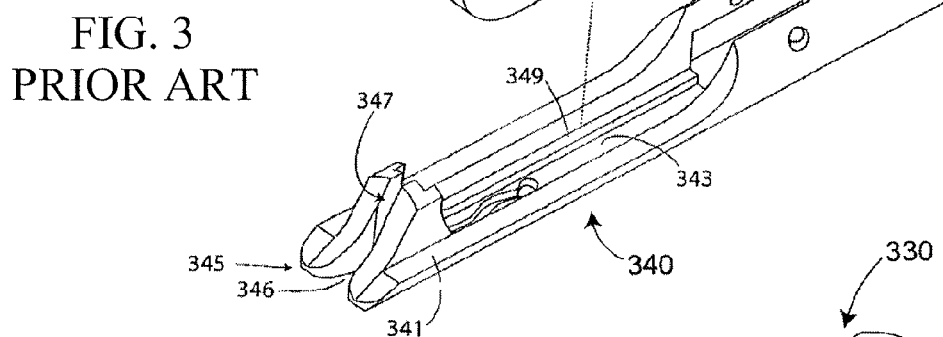
FIG. 3 is a detailed view illustration of the lower jaw of the suture passing instrument of FIG. 1.
Figure 4:
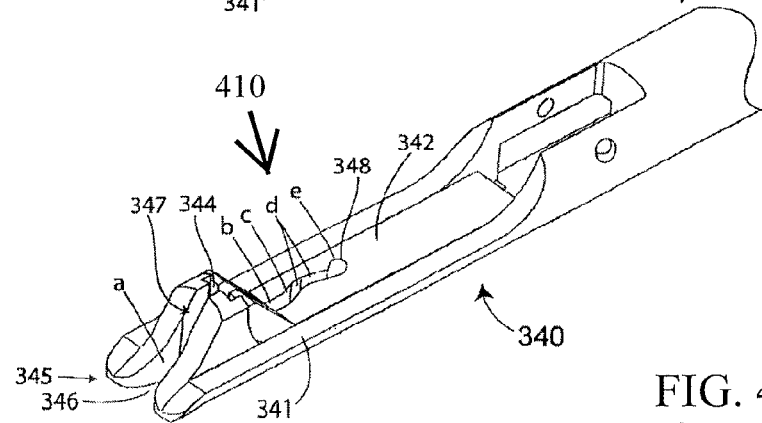
FIG. 4 is an illustration of the lower jaw of the suture passing instrument of FIG. 1 as assembled.

FIGS. 2-4 illustrate in more detail the lower jaw 340 and retaining mechanism 410 of the suture passing instrument shown of FIG. 1. As mentioned above, the lower jaw 340 can include a lower jaw body 341 that is formed as an integral part of the elongate shaft 330 that couples the jaws 314 to the handle assembly 320. The lower jaw 340 can also include a jaw insert 342 that can be removably or permanently attached to the lower jaw body 341. The jaw insert 342 can be configured to rest on ledges 349 formed in the lower jaw body 341 (as shown in FIG. 3) such that the lower jaw body and jaw insert can define a needle channel 343 therebetween. The bendable needle can be configured to rest within the channel 343 and advance distally (or retract proximally) through the channel when deployed by movement of the needle trigger 381. The lower jaw body 341 and jaw insert 342 can include a sloping distal portion that can deflect the bendable needle 400 such that it extends from the suture passing instrument in a direction offset from an elongate axis of the instrument. In one embodiment, the offset can be approximately 90 degrees, such that the needle 400 extends from the instrument in a direction substantially perpendicular to the elongate axis of the instrument.

The lower jaw body 341 and jaw insert 342 can also include features that define a retaining mechanism 410 configured to hold a suture loaded therein before it is passed through tissue disposed between the jaws 314. For example, and as shown in FIGS. 3-4, the lower jaw body 341 can include a forked distal end 345 that includes a suture-loading ingress provided as an end slot 346. The end slot 346 can lead to a suture slot 347 contained in both the lower jaw body 341 and the jaw insert 342. The suture slot 347 can terminate at a proximal end thereof at a suture retention node or slot end 348 where the suture can be frictionally held before being passed through tissue by the bendable needle 400.

An exemplary prior art method for using the suture passing instrument shown in FIGS. 1-4 can begin with loading a portion of a suture strand into the retaining mechanism 410 such that the suture resides at the suture retention node 348. The suture passing instrument can then be inserted into a patient's body and positioned such that tissue is grasped between the jaws 314. The needle movement mechanism 380 can then be actuated to advance the bendable needle 400 distally. As the needle 400 moves toward the distal end of the instrument, the notch 405 formed in a side of the needle can catch the suture residing in the suture retention node 348 and carry it distally along the suture slot 347. As the needle is advanced further, it can extend from the channel exit 344 and pass through the tissue grasped between the jaws 314, carrying the suture with it. After the needle passes entirely through the tissue, it can be retracted into the instrument, leaving behind a loop of suture formed on an opposite side of the tissue from the lower jaw 340. This loop can be grasped by a hook feature on the suture passing instrument (e.g., hook 1010 shown in FIG. 10) or a second tool and pulled to pass the suture through the tissue.

A more detailed explanation of the suture passing instrument 310 and its known method of use can be found in U.S. Pat. No. 7,879,046 to Weinert et al., entitled "Suturing Apparatus and Method," which is hereby incorporated by reference in its entirety. One of skill in the art will appreciate that the suture passing instrument and retaining mechanism described above are just one of a number of devices and mechanisms known in the art. For example, in some embodiments a retaining mechanism can include a suture slot that is offset 90 degrees from the slot 347 shown in FIG. 7 and configured for loading a suture strand on a side of the instrument. A number of variations on the exemplary retaining mechanism described above—as well as other retaining mechanism configurations—are known in the art and the methods described herein need not be limited to the described embodiment of a suture passing instrument and retaining mechanism.

As noted above, a limitation of the suture passing methods known in the prior art is that only a single suture can be passed through tissue before the instrument must be removed from a patient's body and reloaded with a second suture. Many procedures require passing several sutures through tissue at a variety of locations, which can result in several repeated cycles of inserting an instrument into a patient, passing a suture, and removing the instrument to reload it. These repeated cycles add complexity to a surgical procedure, increase the time required to finish the procedure, and also run the risk of suture entanglement with sutures that reside in a cannula or portal used to introduce the instrument into a patient's body. The methods described herein address these problems by passing multiple sutures through tissue without removing the suture passing instrument from a patient's body. In particular, a method is provided that includes double-loading a suture passing instrument, such as the instrument 310 described above, such that two sutures can be passed through tissue at one or more locations without removing the instrument from a patient's body.

Figure 5:
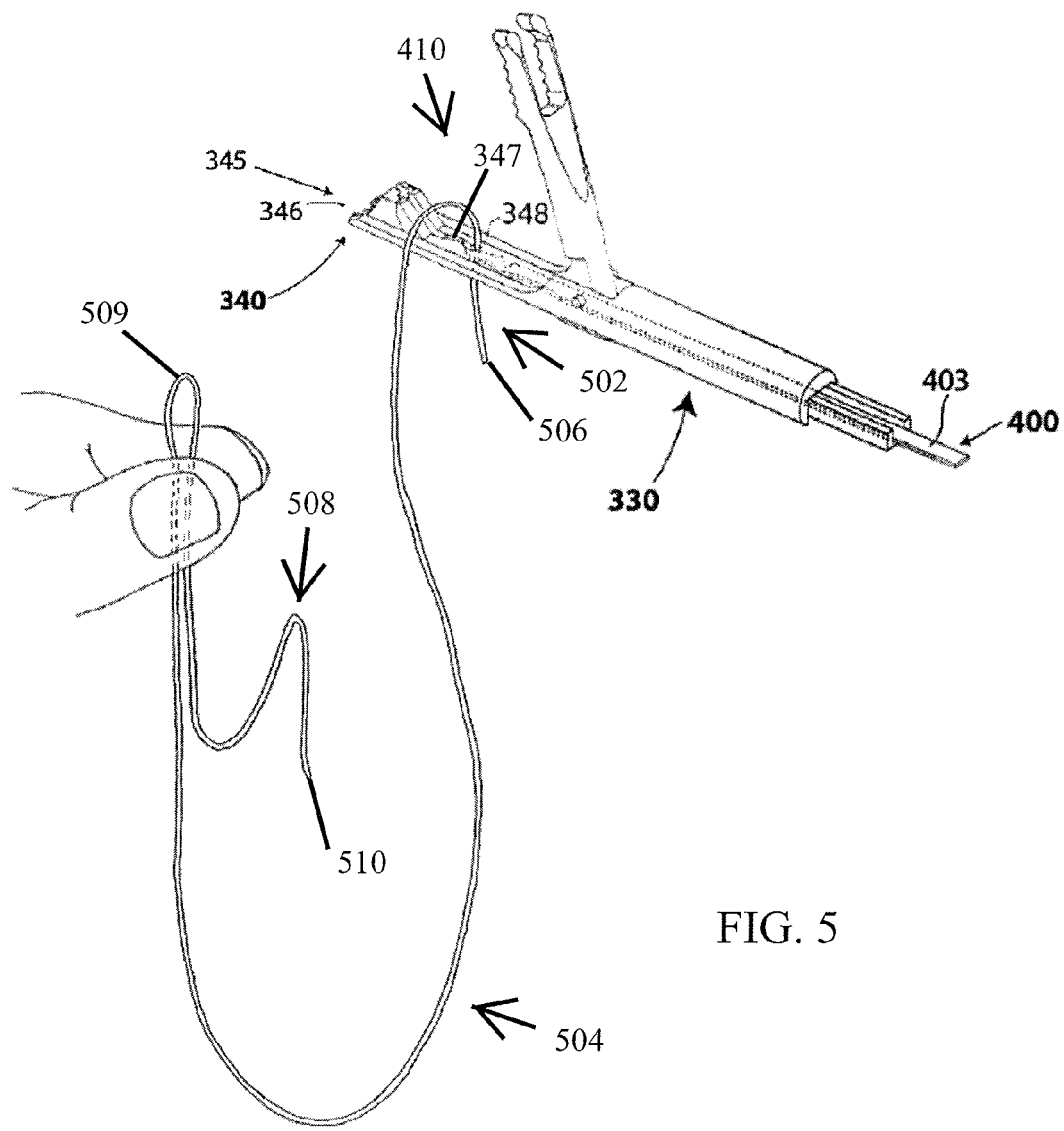
FIG. 5 is an illustration of one embodiment of a first suture limb loaded into a retaining mechanism of a suture passing instrument.

In one embodiment, a method of passing multiple sutures can include loading a first suture limb or portion of suture into a retaining mechanism of a suture passing instrument, as illustrated in FIG. 5. As shown in the figure, a first suture limb 502 of a suture strand 504 can be loaded into a retaining mechanism of a suture passing instrument, such as the retaining mechanism 410 disposed at the distal end of the suture passing instrument 310 described above. In one embodiment, the suture limb 502 can be loaded by passing the suture limb through the forked distal end 345 of the suture passing instrument 310 and pulling the suture limb to the proximal end 348 of the suture slot 347. The first suture limb 502 can be loaded such that a tail end 506 extends from a bottom surface of the suture passing instrument. The first suture limb 502 can be loaded such that the tail end 506 extends from the instrument by a variety of lengths but, in some embodiments, the tail end 506 can extend from the bottom surface of the suture passing instrument by about 10-20 mm.

Figure 6:
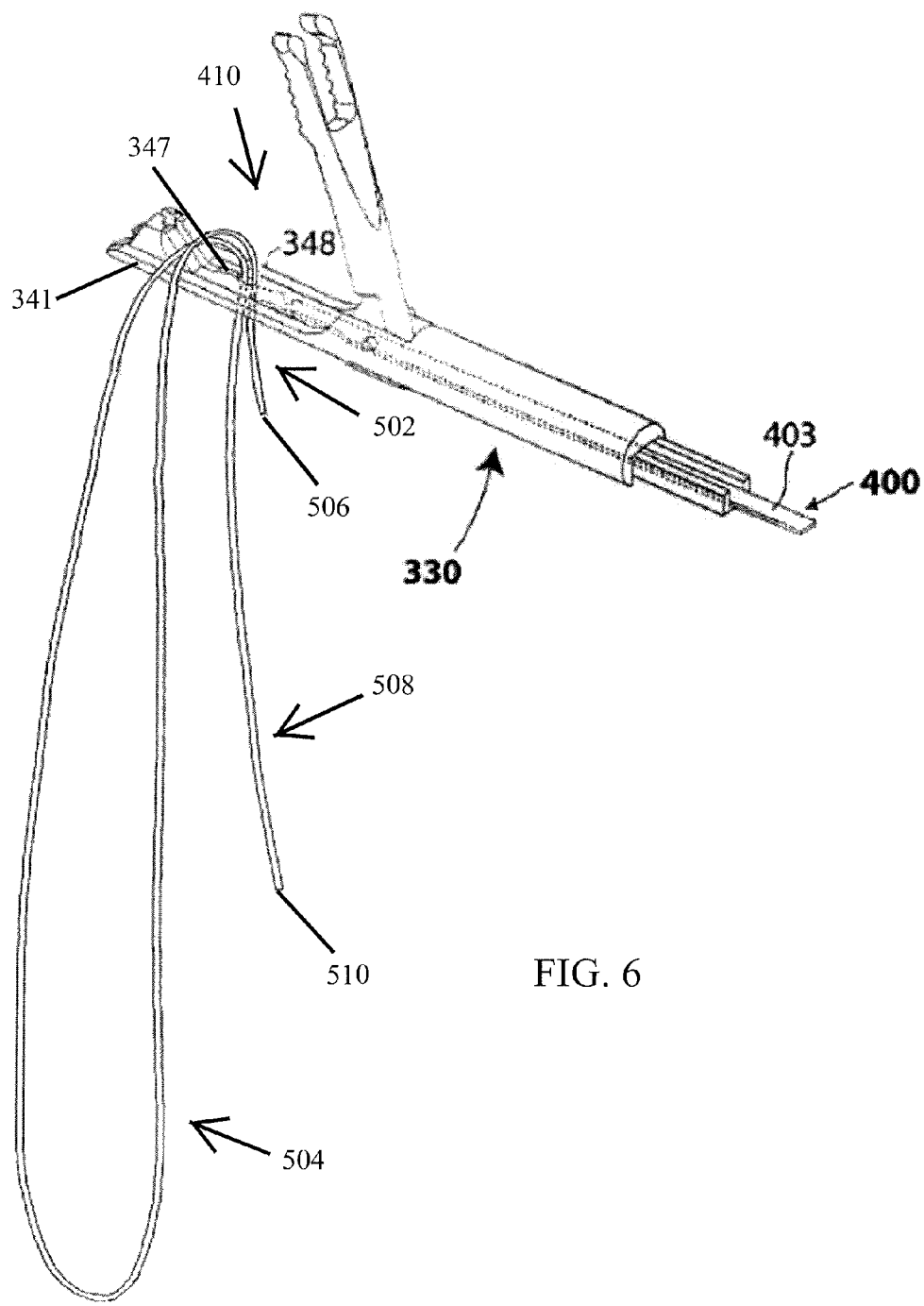
FIG. 6 is an illustration of one embodiment of a second suture limb loaded into the retaining mechanism of the suture passing instrument of FIG. 5.

In order to pass a second suture without removing the instrument from a patient's body, a second suture limb 508 can be loaded into the retaining mechanism of the suture passing instrument prior to inserting the instrument into a patient's body. This can be done, for example, by forming a loop 509 a distance from a tail end 510 of the second suture limb 508 and threading a portion of the second suture limb 508 into the retaining mechanism 410 in a similar manner as the first suture limb 502. As described below in more detail, the loop 509 can be formed at a variety of positions along the length of the suture strand 504 such that the second suture limb 508 extends below the suture passing instrument by a variety of lengths. In some embodiments, the length can be selected such that the tail end 510 of the second suture limb 508 can extend outside of a cannula or portal when the instrument is inserted into a patient's body, thereby allowing a user to manipulate the second suture limb 508 during the procedure. In certain embodiments, the length can be selected such that the tail end 510 of the second suture limb 508 can extend from a cannula or portal by at least about 10-20 mm when the suture passing instrument is inserted into a patient's body. Selecting the length in this manner can result in the second suture loop 508 extending below the suture passing instrument by a greater distance than the first suture limb 502, as shown in FIG. 6. By way of example, in some embodiments, the second suture limb 508 can extend below the suture passing instrument by about 250 mm.

The second suture limb can be, for example, an opposite end of a single suture strand 504, as shown in FIG. 5. For example, opposing end portions of a suture strand 504 having a length of about 910 mm can be the first and second suture limbs 502, 508. In other embodiments, however, the second suture limb can be an end of a second suture strand, as is described in more detail below. Whether using one suture strand or two, the suture limbs 502, 508 can, in some embodiments, be selected from the outer two quarters of a suture strand's length, i.e., portions not within the middle half of the length of the suture. Selecting the first and second suture limbs in this manner can be advantageous as it is possible that the retaining mechanism or other surgical tool could damage the suture during a procedure. As a result, the middle portion of a suture (i.e., the portion that is ultimately left in a patient's body to fix tissue) should be handled as little as possible. Handling the outer portions of a suture can be preferable because they can often be trimmed off at the end of a procedure. It should be appreciated that the exemplary lengths described above can be adjusted in view of this principle if, for example, shorter length suture strands are used. By way of example, the middle portion of a suture strand having an overall length of about 510 mm (as opposed to, e.g., 910 mm or longer) may be damaged by a needle or other surgical tool if the second suture limb is loaded as described above (e.g., the tail end 510 extending about 250 mm from the lower jaw body 341). To avoid this, the second suture limb 508 can be loaded such that the tail end 510 extends below the lower jaw body 341 by a lesser amount in such an embodiment.

As shown in FIG. 6 and mentioned above, the second suture limb 508 can be loaded into the retaining mechanism 410 of the suture passing instrument in the same manner as the first suture limb 502, e.g., such that the suture limb 508 is received within the suture slot 347 of the retaining mechanism 410 and a tail end 510 of the suture limb 508 extends from the bottom surface of the lower jaw body 341 of the suture passing instrument. However, the second suture limb 508 can be loaded such that the second suture limb is seated within the suture slot 347 just distally of the first suture limb 502 that is at the proximal-most end 348 of the slot 347. Also visible in FIG. 6 is the relative difference in lengths between the portions of the first suture limb 502 and the second suture limb 508 extending below the lower jaw body 341 of the suture passing instrument. As shown in the figure, the tail end 510 of the second suture limb 508 can extend from the suture passing instrument by a greater distance than the tail end 506 of the first suture limb 502. As described above, the length of the second suture limb 508 can be selected such that the tail end 506 can extend beyond the proximal end of a cannula or portal when the suture passing instrument is inserted into a patient's body. In addition, a middle portion 512 of the suture strand 504 can make a loop extending from a top surface of the lower jaw of the suture passing instrument.

Figure 7:
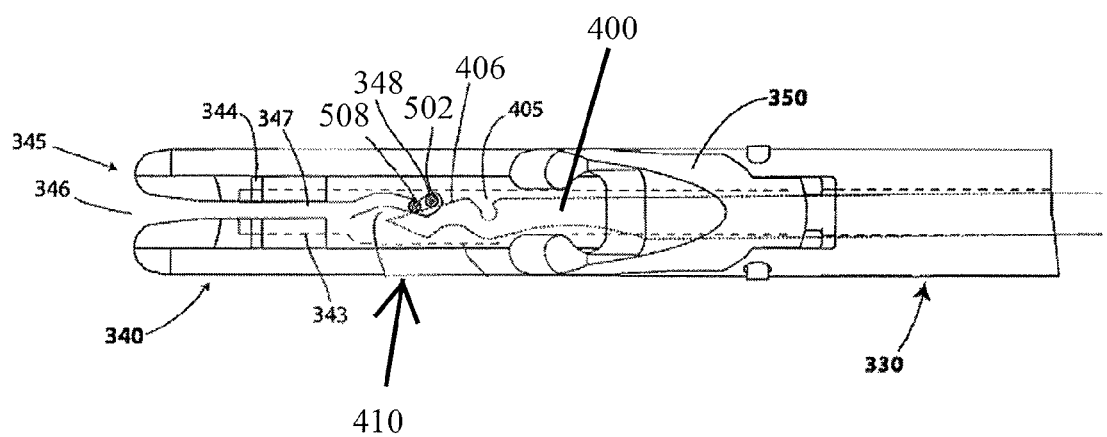
FIG. 7 is a top view illustration of the first and second suture limbs loaded into the retaining mechanism of the suture passing instrument of FIG. 5.

An alternative view of the loading orientation of FIG. 6 is shown in the top view illustration of FIG. 7. As described above, the first suture limb 502 can be loaded into the suture passing instrument such that it resides at a proximal end 348 of a suture slot 347 that forms the retaining mechanism 410 of the instrument. The second suture limb 508 can be loaded into the instrument such that it resides at a location just distal to the first suture limb 502. Also visible in FIG. 7 are the movable jaw 350 (shown in an open configuration) and the bendable needle 400 residing in the needle channel 343. The needle 400 can include a ramp 406 positioned just distal to the notch 405 such that at least the proximal-most suture limb loaded in the retaining mechanism is captured within the notch as the needle 400 is advanced distally through the needle channel 343.

Figure 8:
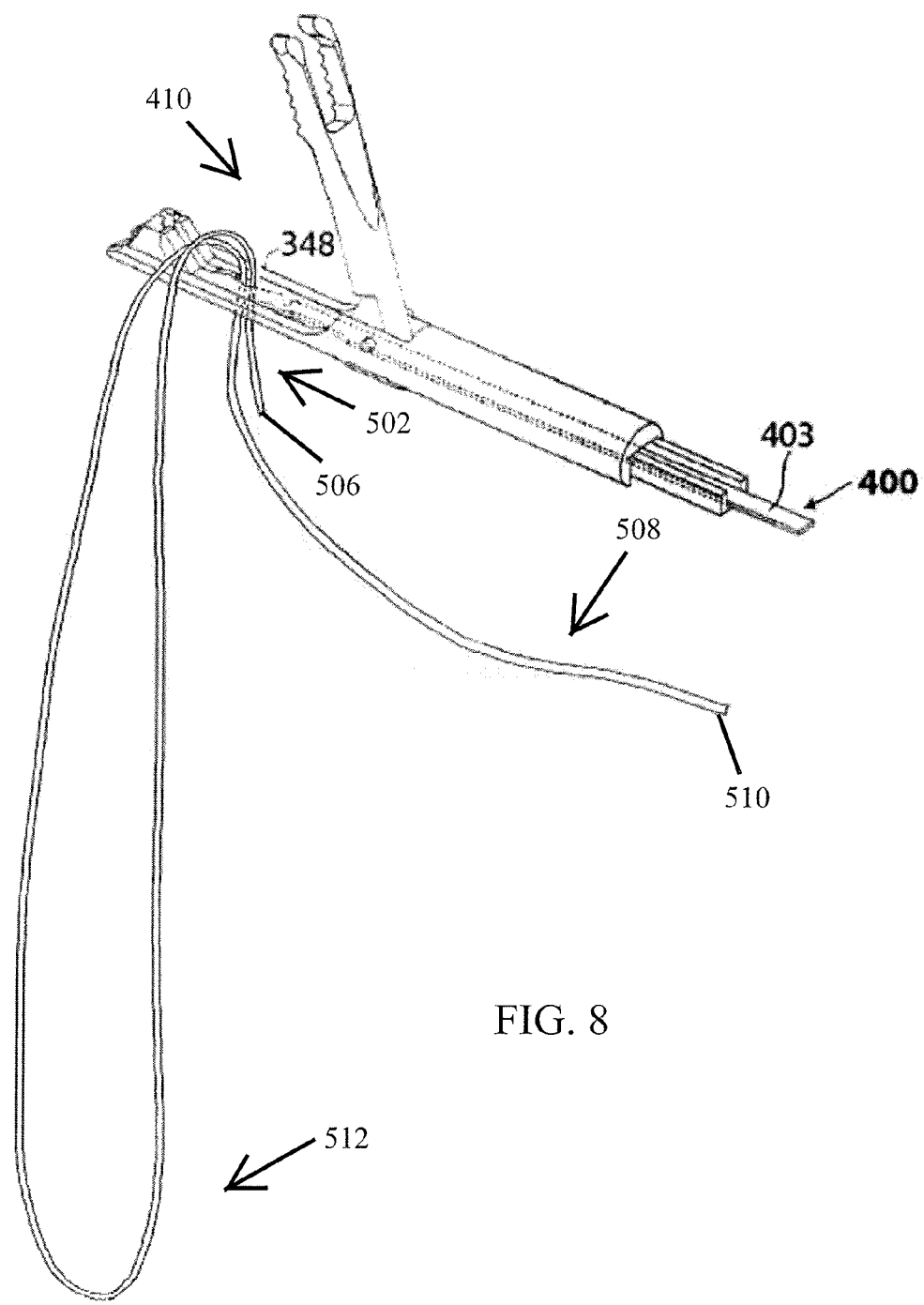
FIG. 8 is an illustration of a second suture limb drawn toward a proximal end of the suture passing instrument of FIG. 5.

The extra length of the second suture limb 508 extending from the suture passing instrument can be utilized in two manners. First, the length of the second suture limb 508 extending below the suture passing instrument can be used to readily distinguish between the first and second suture limbs. In addition, the extended length of the second suture limb 508 can be utilized to remotely reload the suture passing instrument after passing the first suture limb 502 through tissue. For this reason, the second suture limb 508 can be pulled toward the proximal end of the suture passing instrument prior to inserting the instrument into a patient's body, as shown in FIG. 8. In some embodiments, the length of the second suture limb 508 can be selected such that the tail end 510 remains outside the patient's body (e.g., outside a proximal end of a cannula or percutaneous portal used to introduce the instrument into a patient's body) after the suture passing instrument is inserted into the patient's body, allowing it to be easily manipulated by a user. In some embodiments, the length of the second suture limb 508 can be selected such that at least about 10-20 mm of the second suture limb extends outside a patient's body when the instrument is inserted into the patient's body. Having at least this amount of the second suture limb 508 extend outside the patient's body during a procedure can allow a user to easily handle the second suture limb 508 by, for example, pressing the second suture limb against a handle assembly 320 of the suture passing instrument during use.

In certain embodiments, it can be desirable to maintain tension on the second suture limb 508 through portions of the procedure. In particular, it can be desirable to maintain tension on the second suture limb throughout the procedure, except when deploying the needle to pass a suture through tissue. Maintaining tension on the second suture limb 508 can, for example, prevent the second suture limb from becoming entangled with the loop formed by the middle portion 512 of the suture strand 504. In addition, maintaining tension on the second suture limb 508 can remove any slack and prevent the second suture limb from falling out of the retaining mechanism 410 prior to and after deployment of the needle (e.g., when repositioning of the instrument, etc.). To maintain tension on the second suture limb 508, and to keep the second suture limb easy to access when necessary, the second suture limb can be secured outside the patient's body during a procedure. This can be accomplished in a variety of manners, including, for example, by pressing the second suture limb 508 against the handle assembly 320 of the suture passing instrument to maintain its position (e.g., with a finger while using the instrument). In certain embodiments, a feature can be provided on the handle assembly 320 or the elongate shaft 330 that allows a user to affix the second suture limb 508 to the suture passing instrument such that the tail end 510 remains accessible throughout a procedure. Exemplary features include a protrusion, eye, or other tie-off. In other embodiments, the second suture limb 508 can be secured to another device outside the patient's body, such as an access port or other feature on a cannula, etc. In still other embodiments, a suture passing instrument can be provided with a tensioning wheel or other spring-loaded tensioning mechanism that can pull the second suture limb 508 toward the proximal end of the suture passing instrument when desired. Such a device can be placed at any location proximal to the retaining mechanism at the distal end of the instrument and, if capable of applying sufficient tension to the second suture limb 508, need not be at a location that remains outside the patient's body.

Figure 9:
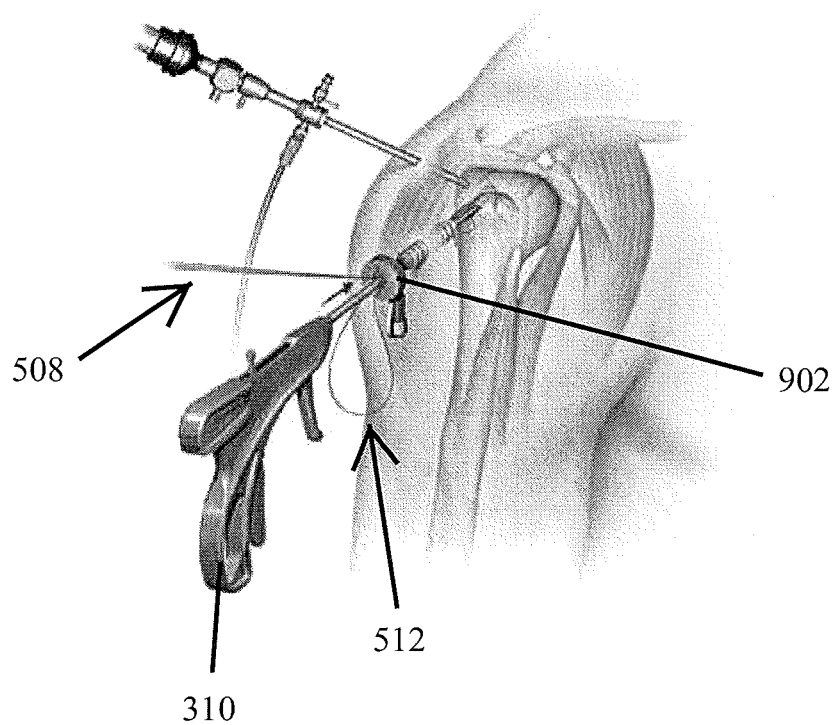
FIG. 9 is an illustration of one embodiment of a suture passing instrument being inserted into a patient's body.

After loading the first and second suture limbs 502, 508 into the retaining mechanism 410 of the suture passing instrument 310, the jaws 314 can be closed to lower the profile of the suture passing instrument and the instrument can be inserted into a patient's body. The instrument can be inserted into the body using any known method for introducing surgical tools. In some embodiments, as shown in FIG. 9, the instrument 310 can be inserted into the patient's body through a cannula 902. In addition, the instrument can be positioned within a patient's body at a variety of sites. In the embodiment illustrated in FIG. 9, the instrument is shown positioned near a patient's shoulder to pass sutures through the muscle and tendon that form the patient's rotator cuff. Also visible in FIG. 9 is the second suture limb 508 and the loop formed by the middle portion 512 of the suture strand 504 extending back out of the cannula 902.

Although cannulas are often used to define a channel through which the procedure can be performed, the cannula is not shown in FIGS. 10-13, 15, and 16 for ease of illustration. Accordingly, to the extent that the figures show components that pass through a patient's skin, these components would typically extend through a cannula, which itself can be passed through the patient's skin. Furthermore, certain embodiments of a suture passing instrument can be inserted into a patient's body through a percutaneous insertion portal (e.g., an opening formed in the tissue using an obturator). The methods described herein can be particularly suited to use through such a portal or opening formed in the skin because they can avoid problems encountered with prior art suturing methods. For example, prior art suturing methods can create a problem known as "bridging" if a suture passing instrument finds a slightly different path through a patient's skin and tissue when reinserted to pass a second suture (i.e., the suture can trap the tissue between the two entry paths). The methods described herein can avoid bridging tissue because the suture passing instrument need not be removed between consecutive suture passes. Still further, although the methods described herein are particularly useful for minimally invasive surgery, such as arthroscopic surgery, they can also be used in open surgical procedures.

Once the suture passing instrument 310 is introduced into the patient's body through a cannula or other mechanism, the movable jaw 350 can be opened and the instrument can be positioned such that tissue is disposed between the jaws 314. In some embodiments, the second suture limb 508 can be tensioned at this time to remove any slack that may have formed and ensure that the second suture limb 508 is seated in a proximal portion of the retaining mechanism adjacent to the first suture limb 502. A user can then actuate the jaw movement mechanism 360 to close movable jaw 350, thereby clamping tissue between the movable jaw 350 and the lower jaw 340.

Figure 10:
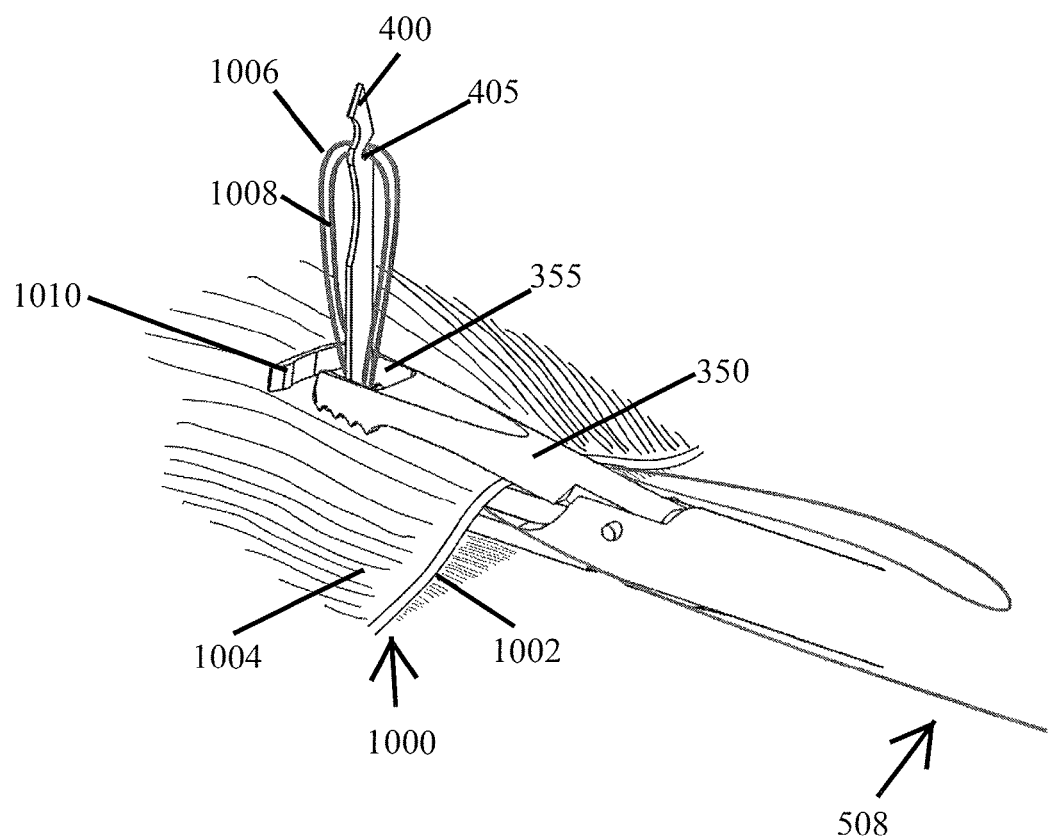
FIG. 10 is an illustration of one embodiment of a needle passing through tissue and carrying portions of first and second suture limbs through the tissue.
Figure 13:
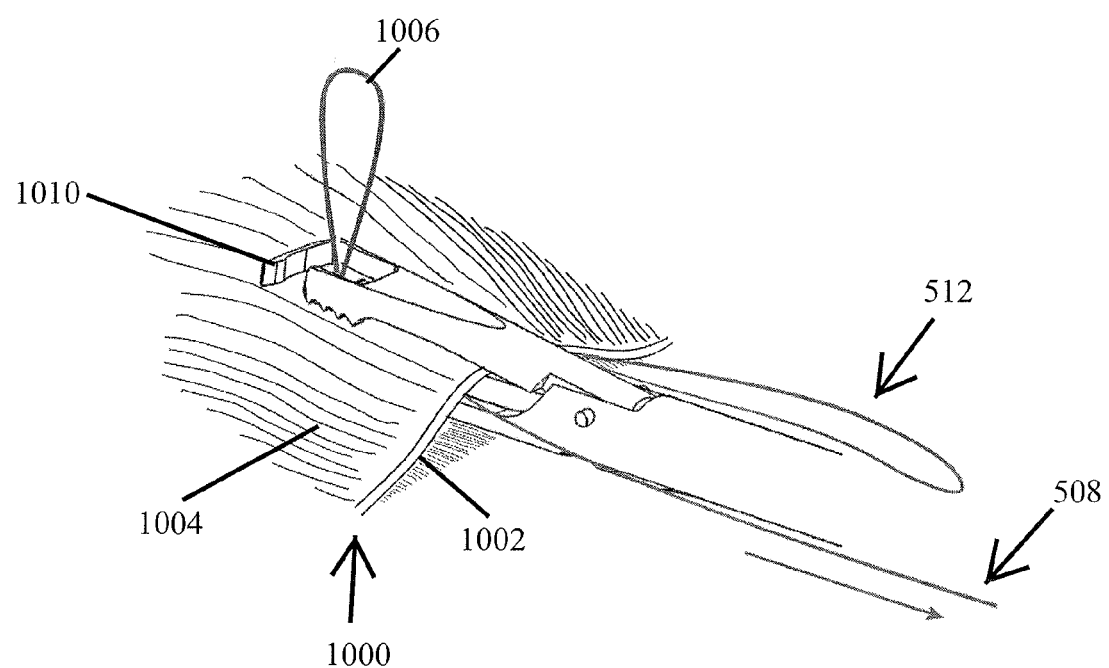
FIG. 13 is an illustration of one embodiment of a second suture limb pulled toward a proximal end of a suture passing instrument until a single suture loop remains on a tissue surface.

The needle movement mechanism 380 can then be actuated to deploy the bendable needle from the distal end of the suture passing instrument 310 and carry a portion of at least the first suture limb 502 through the tissue grasped between the jaws 314. As noted above, any tension on the second suture limb 508 can be released prior to actuating the needle movement mechanism 380, thereby allowing the needle to deploy without encountering resistance. FIG. 10 illustrates a suture passing instrument 310 with a needle 400 in a deployed position. In this configuration, the needle 400 extends out of the channel exit 344 on the lower jaw 340 (not shown), through the tissue 1000, and through the opening 355 formed in the movable jaw 350. As shown in the figure, the notch 405 of the bendable needle 400 can carry portions of both the first and second suture limbs 502, 508 through the tissue such that the tail ends of the first and second suture limbs 506, 510 extend from a first surface 1002 of the tissue 1000 and first and second suture loops 1006, 1008 are formed on a second surface 1004 of the tissue 1000 that is opposite from the first surface 1002. The needle 400 may not always carry both suture limbs 502, 508 through the tissue, so in some embodiments only a single suture loop 1006 may be formed on second surface 1004 of the tissue 1000, as shown in FIG. 13.

Figure 11:
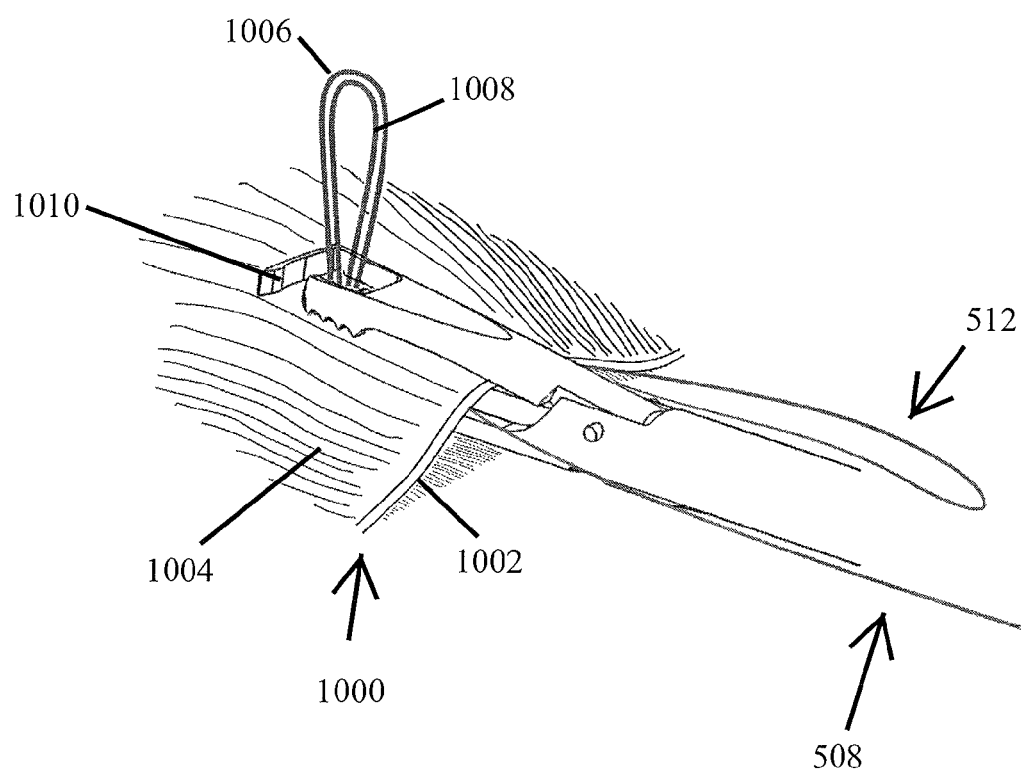
FIG. 11 is an illustration of first and second suture loops formed on a tissue surface after the needle of FIG. 10 is retracted into the suture passing instrument.

Following deployment, the needle can be retracted into the suture passing instrument 310. The notch 405 can be configured to carry the first and/or second suture limbs 502, 508 only when being extended such that retracting the needle 400 can leave the first and second suture loops 1006, 1008 undisturbed, as shown in FIG. 11. Also visible in FIG. 11 is the second suture limb 508 extending toward a proximal end of the suture passing instrument, and the large loop formed by the middle portion 512 of the suture strand 504. As mentioned above, the middle portion 512 can hang freely or can extend toward the proximal end of the suture passing instrument with the second suture limb 508. In some embodiments, the middle portion 512 can be long enough that it extends through the cannula used to introduce the suture passing instrument 310 and outside of the patient's body.

Figure 14:
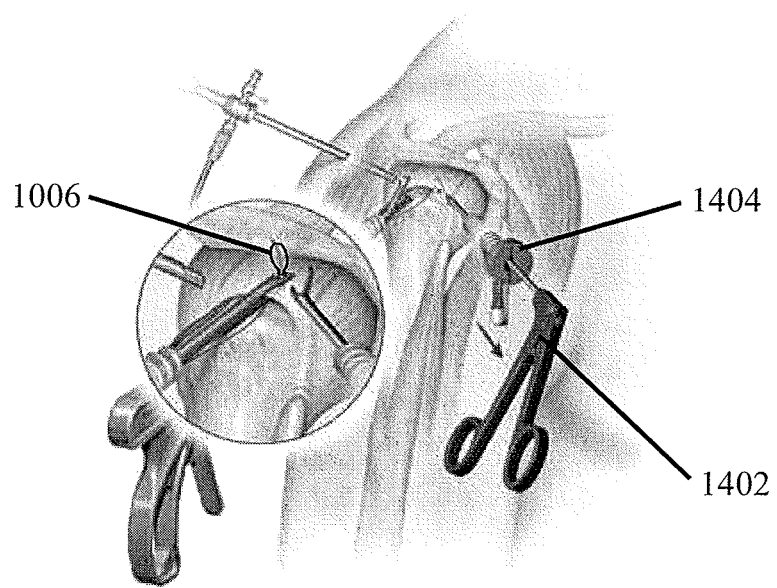
FIG. 14 is an illustration of one embodiment of a suture grasper manipulating a suture loop passed through tissue by a suture passing instrument.
Figure 15:
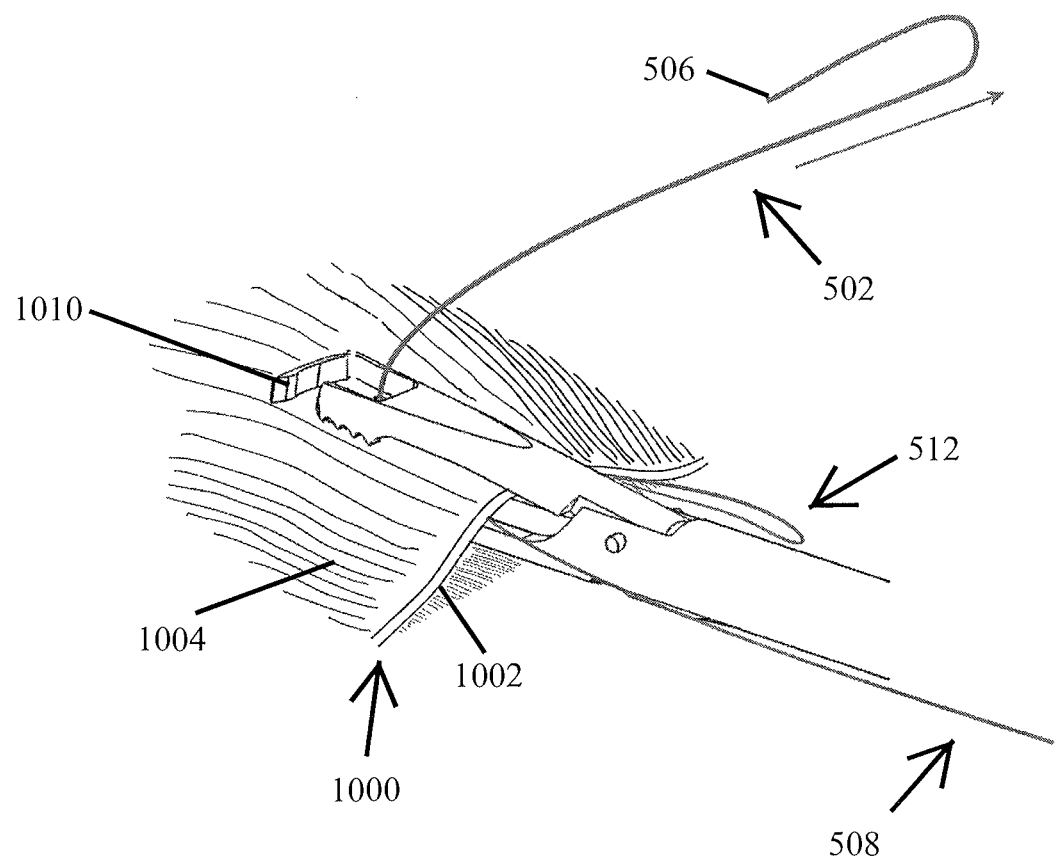
FIG. 15 is an illustration of one embodiment of a first suture limb pulled through tissue.
Figure 16:
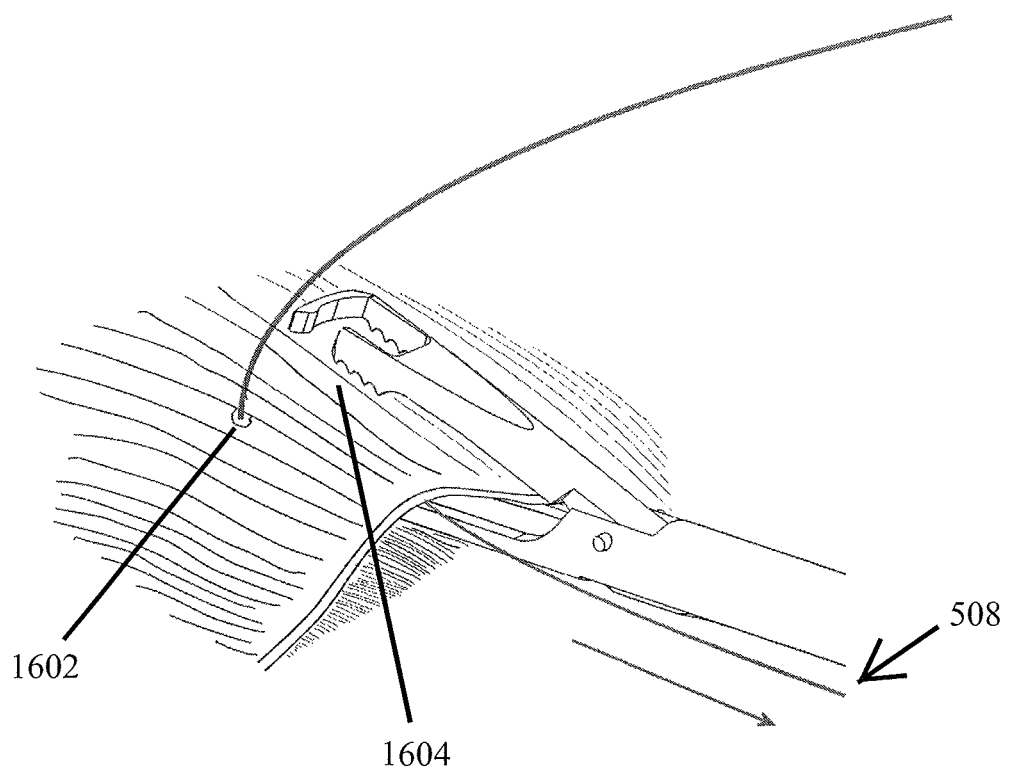
FIG. 16 is an illustration of one embodiment of a suture passing instrument reloaded and repositioned in advance of passing a second suture limb through tissue.

After the needle is retracted, it is possible that two substantially equally-sized suture loops 1006, 1008 are formed on the second surface 1004 of the tissue 1000. However, it is also possible that one suture loop is larger than the other, or that only a single suture loop is formed on the second surface 1004. If only a single suture loop is formed on the second surface, as shown in FIG. 13, the needle carried only the first suture limb 502 through the tissue. In such a case, tension is applied to the second suture limb 508 (to prevent it from being pulled through with the first suture limb) and a grasper tool can be used to grasp the suture loop and pull it until the tail end 506 of the first suture limb 502 comes through the tissue. FIG. 14 illustrates one embodiment of a grasper tool 1402 being inserted into a patient's body using a second cannula 1404 and grasping a first suture loop 1006. Once the suture loop is grasped, the grasper tool 1402 can be withdrawn from the patient's body to pull the first suture limb 502 through the tissue, as shown in FIG. 15. In some embodiments, the first suture limb 502 can be drawn through an ancillary portal (e.g., second cannula 1404) outside of the patient's body for ease of suture management. In other embodiments, the hook feature 1010 of the upper jaw 350 can be utilized in place of a grasper tool to draw the first suture limb 502 through the tissue 1000.

Figure 12:
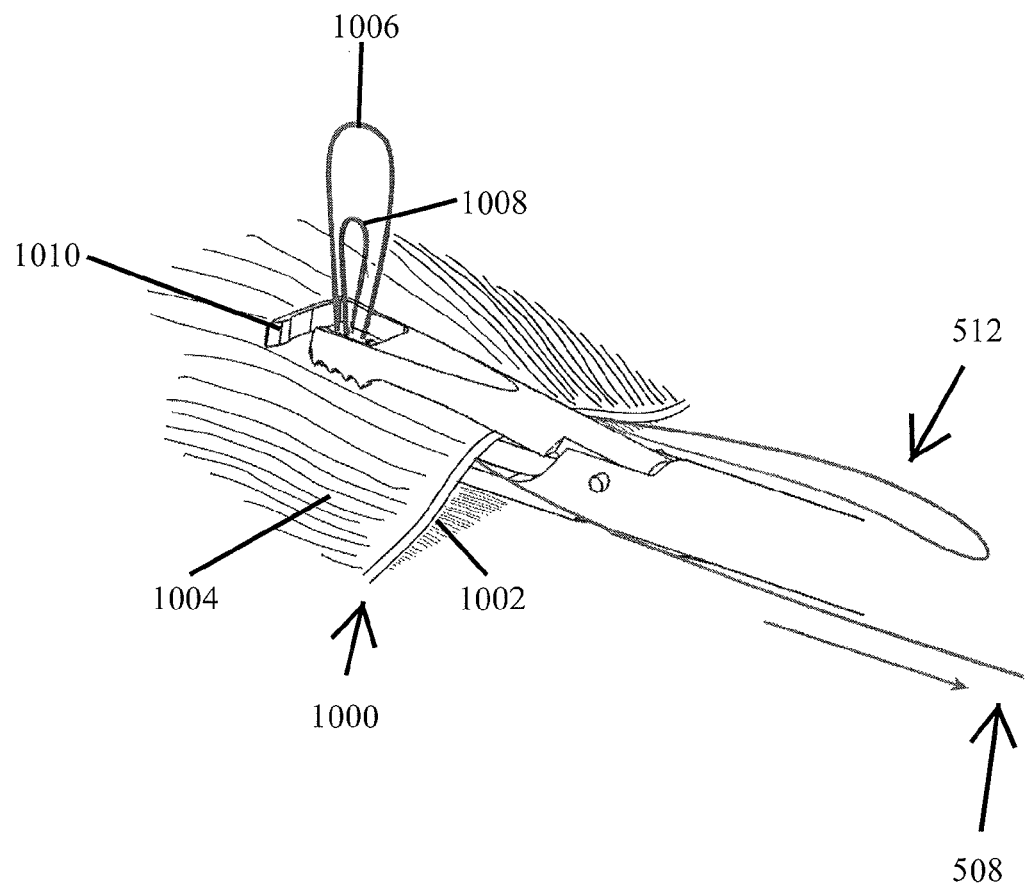
FIG. 12 is an illustration of one embodiment of determining which of two suture loops is a first suture loop by pulling a second suture limb toward a proximal end of a suture passing instrument.

If two suture loops are present, as shown in FIG. 11, the method can include determining which of the two suture loops 1006, 1008 corresponds to the first suture limb 502 by pulling the second suture limb 508 toward a proximal end of the suture passing instrument, as shown by the arrow in FIG. 12. Pulling on the second suture limb 508 draws the second suture limb in a proximal direction and reduces the size of the second suture loop 1008 formed on the second surface 1004 of the tissue 1000. The second suture limb 508 can be pulled until the second suture loop 508 retracts through the tissue 1000 completely, leaving the first suture loop 1006 alone, as shown in FIG. 13. A suture grasper or other tool can then be inserted as described above and used to pull the first suture loop 1006 until the tail end 506 of the first suture limb 502 passes through the tissue 1000. If the first suture limb 502 is pulled further, the middle portion 512 of the suture strand 504 can begin to pass through the tissue, thereby shortening the size of the loop formed by the middle portion 512 of the suture strand, as shown in FIG. 15. In some embodiments, the first suture limb 502 can be pulled far enough that the middle portion 512 of the suture strand 504 is contained within a cannula used to introduce the instrument and does not extend outside the body before proceeding to pass a second suture through tissue.

After passing the first suture limb 502 through the tissue 1000, the suture passing instrument can be remotely reloaded without removing the device from the patient's body. To reload, the second suture limb 508 can be pulled toward a proximal end of the suture passing instrument such that the second suture limb 508 is moved proximally within the retaining mechanism 410 of the instrument, as shown by the arrow in FIG. 16. In other words, the second suture limb 508 can be pulled proximally such that it resides in the proximal end 348 of the suture slot 347 that was previously occupied by the first suture limb 502. In addition, the suture passing instrument 310 can be repositioned at this time to pass the second suture limb 508 through tissue 1000 at a different location than the first suture limb 502. This can be accomplished by opening the jaws 314 and moving the suture passing instrument from a first location 1602 to a second location 1604, while simultaneously keeping a light tension on the second suture limb 508 to prevent it from falling out of the suture slot 347. Alternatively, the suture passing instrument need not be repositioned and the second suture limb 508 can be passed through the tissue at the same location as the first suture limb 502, thereby reducing the number of holes formed in the tissue. Regardless of whether or not the suture passing instrument is repositioned, in some embodiments the jaws 314 can be at least partially opened to remove any resistance to the movement of the second suture limb 508 and reduce the possibility of the jaws 314 damaging the suture strand 504. For example, in some embodiments, the jaws can be opened a small amount to allow the second suture limb 508 to move without resistance while preventing the repositioning of the suture passing instrument with respect to the tissue.

Passing the second suture limb 508 after remotely reloading the suture passing instrument involves repeating the steps detailed above for deploying the needle, retracting the needle, and grasping a suture loop formed on the second surface 1004 of the tissue 1000 to draw the tail end 510 of the second suture limb 508 through the tissue, as shown in FIGS. 10 and 13-15. However, in some embodiments, a different tool can be used to grasp the suture loop and draw the second suture limb 508 through the tissue 1000. In particular, in some embodiments a looping device or other suture manipulator configured to allow the second suture limb 508 to slide across the manipulator can be utilized in place of a grasper configured to rigidly grip the second suture limb. Such a device can be preferable because, in the case of the second suture limb 508, there can be a large amount of suture that must be pulled through the tissue 1000 before the tail end 510 of the second suture limb 508 passes through the tissue (i.e., the extra length of the second suture limb 508 extending outside of the patient's body must be drawn into the patient's body and through the tissue). Using a grasper that does not slide along the suture strand to draw this extra length through the tissue can simultaneously pull the first suture limb 502 back into the patient's body through the ancillary portal (e.g., second cannula 1404). By contrast, if a looping device or other sliding suture manipulator is used, the first suture limb 502 can be secured outside the body (e.g., by holding the suture or even by the friction from the second cannula's seals) such that it is not drawn back into the patient's body. In addition, before pulling the suture loop to draw the second suture limb 508 through the tissue, any tension maintained on the second suture limb 508 can be released to allow the second suture limb 508 to be pulled into the patient's body and through the tissue.

Figure 17A:
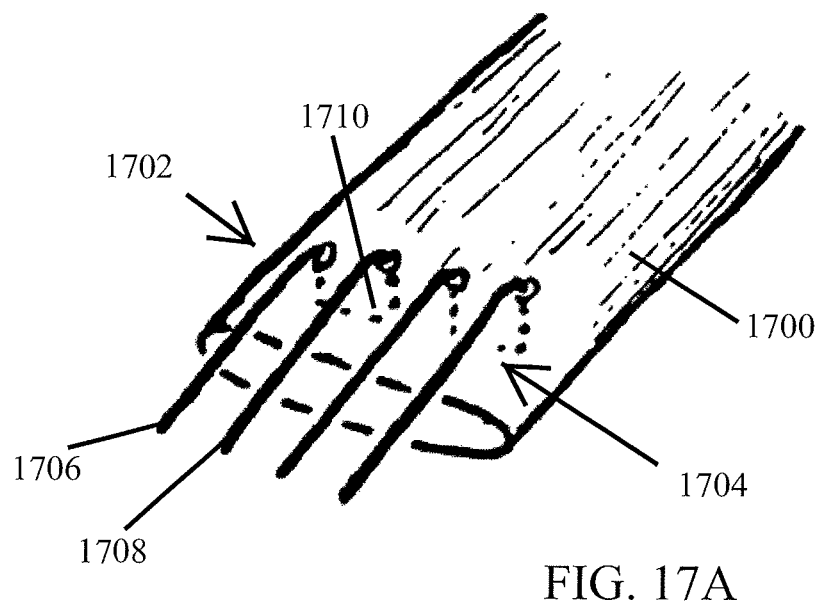
FIG. 17A is an illustration of two inverted mattress stitches in tissue.

If the first and second suture limbs 502, 508 are opposite ends of a single suture strand 504, as shown in FIGS. 5-16, the end result will be an inverted mattress stitch formed in the tissue 1000. FIG. 17A illustrates two inverted mattress stitches 1702, 1704 formed side-by-side in tissue 1700. The mattress stitch 1702 is formed by passing opposing ends 1706, 1708 through the tissue from an underside thereof at different locations. This leaves the opposing ends 1706, 1708 free on a top surface of the tissue 1700, and a middle portion 1710 connecting the ends on a bottom surface of the tissue (shown in phantom). The second inverted mattress stitch 1704 is formed in a similar manner.

The methods described herein can also be utilized to form a number of other stitching patterns. For example, it is possible that the orientation of the suture passing instrument can be reversed to form a traditional mattress stitch (i.e., the tail ends of the suture strand extend below the tissue with a middle portion connecting them on a top surface of the tissue). However, in many cases this is not possible due to space constraints on the underside of the tissue. For example, in a rotator cuff repair procedure, the muscle and tendon of the rotator cuff lies against the underlying bone. Deploying a needle from the suture passing instrument so as to create a mattress stitch can result in injury to the bone from contact with the needle tip. This could be achieved, however, with a shorter length needle (e.g., a needle that does not extend as far from the suture passing instrument when in the fully deployed state). The methods described herein can also be used in forming a number of variations on the mattress stitch, such as an inclined mattress stitch and a Mason-Allen stitch.

Figure 17B:
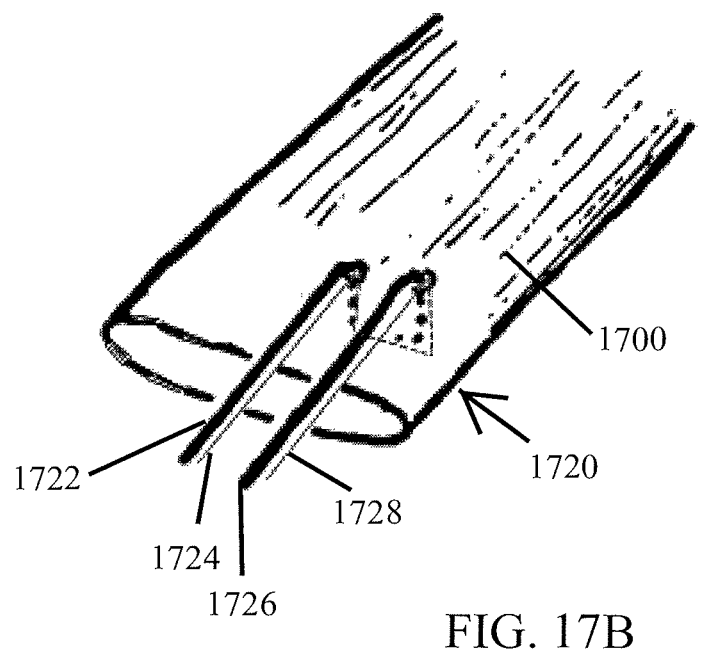
FIG. 17B is an illustration of a double-width inverted mattress stitch in tissue.

In other embodiments, the suture passing instrument can be loaded with suture limbs from two separate suture strands. This configuration can be used, for example, to form a double-width inverted mattress stitch, as shown in FIG. 17B. The double-width inverted mattress stitch 1720 can be formed by passing first suture limbs 1722, 1724 from two separate suture strands through tissue 1700 at a first location. The suture passing instrument can then be removed from the patient's body and loaded as described above with second suture limbs 1726, 1728 that are the opposite ends of the two separate suture strands. The suture passing instrument can be reintroduced into a patient's body and the second suture limbs 1726, 1728 can be passed through the tissue 1700 at a second location using the methods described above. In such an embodiment, the need to remove and reintroduce the suture passing instrument into the patient's body is not eliminated entirely, but is reduced significantly to minimize the complexity and time required to form this type of stitch.

Figure 18A:
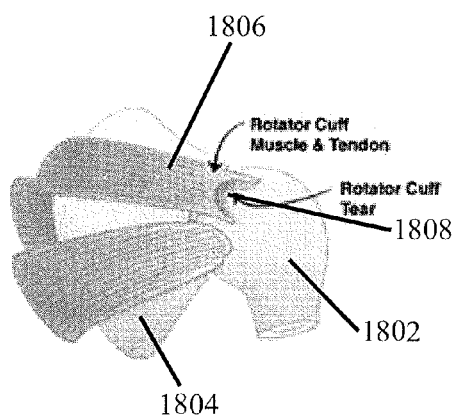
FIGS. 18A-18D illustrate one embodiment of a rotator cuff repair procedure that can be performed using the suture passing methods of the present invention.
Figure 18B:
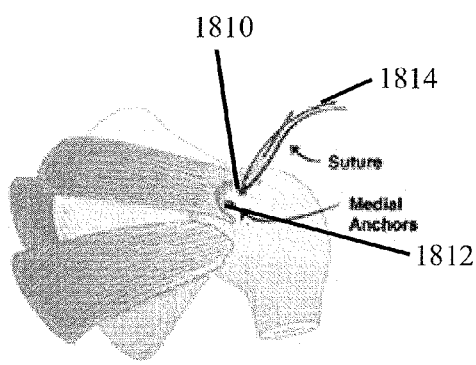
Figure 18C:
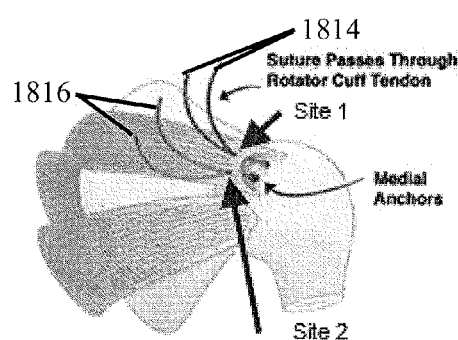

The methods described herein can be utilized in a number of different surgical procedures at a variety of locations within a patient's body. In one embodiment, the methods can be utilized in repairing a rotator cuff tear in a patient's shoulder. FIGS. 18A-18D illustrate one embodiment of a "spanning technique" method for repairing a rotator cuff tear utilizing the suture passing methods described herein. FIG. 18A shows a patient's humerus 1802 and scapula 1804, along with the muscle and tendon that form the rotator cuff 1806. A tear 1808 is present in the muscle and/or tendon 1806. To repair the tear and fix the muscle to the humerus 1802, medial anchors 1810, 1812 can be used to secure two suture strands 1814, 1816 to the humerus, thereby creating four free ends of suture that are anchored to bone. In some embodiments, however, only a single medial anchor (e.g., anchor 1810) can be used. The four free ends of the two suture strands 1814, 1816 can be passed through the muscle and tendon of the rotator cuff 1806 using the methods described herein. For example, the two free ends of the suture 1814 can be loaded as the first and second suture limbs 502, 508 and passed through the tissue 1806 in one location, and then the method can be repeated using the two free ends of the suture 1816, as shown in FIG. 18C. In some embodiments, however, the two free ends of the suture 1814 can be passed through tissue in different locations (e.g., at two locations spaced apart by 4-6 mm). In such an embodiment, the same process can be repeated for two free ends of the suture 1816.

Figure 18D:
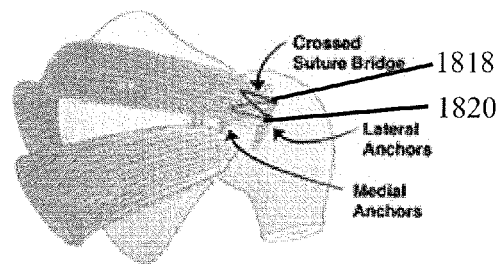

The four free ends of the two suture strands 1814, 1816 can then be manipulated to move the rotator cuff muscle and tendon 1806 into a desired location. The free ends of the suture strands can be "spanned" across and secured to a second set of anchors 1818, 1820 in a number of manners known in the art, as shown in FIG. 18D. Of course, this is just one embodiment of a possible method for repairing a rotator cuff tear. In other embodiments, the tear can be repaired using one or more inverted mattress stitches, double-width inverted mattress stitches, or Mason-Allen stitches.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A method of passing a suture through tissue, comprising:
    loading a first suture limb of a suture strand into a retainer disposed at a distal end of a suture passing instrument such that the first suture limb extends on a first side of the instrument;
    loading a second suture limb of the suture strand into the retainer of the suture passing instrument such that the second suture limb extends on the first side of the instrument, the first and second suture limbs being opposite ends of the suture strand;
    positioning first and second jaws of the suture passing instrument to grasp tissue within a patient's body;
    deploying a needle from the suture passing instrument such that the needle extends through the tissue grasped between the first and second jaws of the instrument, the needle carrying a portion of at least the first suture limb through the tissue such that the first and second suture limbs extend from a first tissue surface and at least a first suture loop is formed on a second tissue surface opposite the first tissue surface;
    pulling the first suture loop to draw the first suture limb through the tissue;
    pulling the second suture limb toward a proximal end of the suture passing instrument to draw the second suture limb into a proximal end of the retainer without removing the suture passing instrument from the patient's body;
    deploying the needle from the suture passing instrument a second time to carry a portion of the second suture limb through the tissue such that the second suture limb extends from the first tissue surface and a second suture loop is formed on the second tissue surface; and
    pulling the second suture loop to draw the second suture limb through the tissue.

2. The method recited in claim 1, wherein the second suture limb extends farther from the suture passing instrument than the first suture limb.

3. The method recited in claim 1, wherein the first suture limb extends from the suture passing instrument by about 10-20 mm.

4. The method recited in claim 1, wherein the second suture limb extends from the suture passing instrument by about 250 mm.

5. The method recited in claim 1, wherein positioning the first and second jaws of the suture passing instrument comprises inserting the instrument into a patient's body, opening the jaws to receive tissue therebetween, and closing the jaws to grasp the tissue.

6. The method recited in claim 5, wherein the instrument is inserted into the patient's body through a cannula.

7. The method recited in claim 1, further comprising retracting the needle following deployment such that the needle retracts into the suture passing instrument without moving the first or second suture limbs.

8. The method recited in claim 1, further comprising, prior to pulling the first suture loop, determining which of two suture loops is the first suture loop by pulling the second suture limb toward a proximal end of the suture passing instrument to reduce the size of a second suture loop formed on the second tissue surface.

9. The method recited in claim 1, further comprising at least partially opening the first and second jaws prior to pulling the second suture limb toward a proximal end of the instrument to permit easier movement of the second suture limb with respect to the retainer.

10. The method recited in claim 1, further comprising repositioning the suture passing instrument without removing the instrument from the patient's body before deploying the needle a second time such that the second suture limb is passed through tissue at a different location than the first suture limb.

11. The method recited in claim 10, wherein repositioning the suture passing instrument comprises opening the first and second jaws to release the tissue grasped therebetween, moving the instrument to receive a different portion of tissue between the first and second jaws, and closing the first and second jaws to grasp the different portion of tissue therebetween.

12. The method recited in claim 1, wherein the suture passing instrument is not repositioned between the first and second deployments of the needle such that both the first and second suture limbs extend through a single hole formed in the tissue.

13. The method recited in claim 1, further comprising placing tension on the second suture limb at a location proximal to the retainer, the second suture limb being pulled toward a proximal end of the instrument.

14. The method recited in claim 1, further comprising attaching the first and second suture limbs to a bone anchor.

15. A method of passing a suture through tissue, comprising:
    loading a first suture limb into a retainer disposed at a distal end of a suture passing instrument such that the first suture limb extends on a first side of the instrument;
    loading a second suture limb into the retainer of the suture passing instrument such that the second suture limb extends on the first side of the instrument;
    positioning first and second jaws of the suture passing instrument to grasp tissue within a patient's body;
    deploying a needle from the suture passing instrument such that the needle extends through the tissue grasped between the first and second jaws of the instrument, the needle carrying a portion of at least the first suture limb through the tissue such that the first and second suture limbs extend from a first tissue surface and at least a first suture loop is formed on a second tissue surface opposite the first tissue surface;
    pulling the first suture loop to draw the first suture limb through the tissue;
    pulling the second suture limb toward a proximal end of the suture passing instrument to draw the second suture limb into a proximal end of the retainer without removing the suture passing instrument from the patient's body;

deploying the needle, from the suture passing instrument a second time to carry a portion of the second suture limb through the tissue such that the second suture limb extends from the first tissue surface and a second suture loop is formed on the second tissue surface;

pulling the second suture loop to draw the second suture limb through the tissue; and repeating the steps above using the opposite ends of the separate suture strands as the first and second suture limbs;

wherein the first and second suture limbs are ends of separate suture strands.

16. A method of passing a suture through tissue, comprising:

loading first and second suture limbs of a suture strand into a retainer of a suture passing instrument such that the first and second suture limbs extend from a first side of the instrument, the first and second suture limbs being opposite ends of the suture strand;

inserting the suture passing instrument into a body of a patient;

positioning first and second jaws of the suture passing instrument to grasp tissue therebetween;

actuating the suture passing instrument to pass a portion of at least the first suture limb through the tissue grasped between the first and second jaws such that the first and second suture limbs extend from a first tissue surface and at least a first suture loop is formed on a second, opposite tissue surface;

pulling the first suture loop to draw the first suture limb through the tissue;

pulling the second suture limb toward a proximal end of the suture passing instrument to draw the second suture limb into a proximal end of the retainer without removing the suture passing instrument from the patient's body;

actuating the suture passing instrument a second time to pass a portion of the second suture limb through the tissue grasped between the first and second jaws such that the second suture limb extends from the first tissue surface and a second suture loop is formed on the second tissue surface; and pulling on the second suture loop to draw the second suture limb through the tissue.

17. The method recited in claim 16, further comprising, prior to pulling the first suture loop, determining which of two suture loops is the first suture loop by pulling the second suture limb toward a proximal end of the suture passing instrument to reduce the size of a second suture loop formed on the second tissue surface.

18. The method recited in claim 16, further comprising repositioning the suture passing instrument without removing the instrument from the patient's body before actuating the instrument a second time such that the second suture limb is passed through tissue at a different location than the first suture limb.

* * * * *